United States Patent [19]

Shah

[11] Patent Number: 4,693,887

[45] Date of Patent: Sep. 15, 1987

[54] MICROPHASE SEPARATED HYDROGELS FOR CONTROLLED RELEASE OF BIOACTIVE MATERIALS

[75] Inventor: Kishore R. Shah, Chelmsford, Mass.

[73] Assignee: The Kendall Company, Boston, Mass.

[21] Appl. No.: 606,794

[22] Filed: May 3, 1984

Related U.S. Application Data

[63] Continuation-in-part of Ser. No. 532,643, Sep. 15, 1983, abandoned.

[51] Int. Cl.[4] .......................... A61K 9/22; A61K 9/52; A61K 31/78; A61K 31/79
[52] U.S. Cl. ........................................ 424/19; 424/80; 424/81
[58] Field of Search .............................. 424/19, 80, 81

[56] References Cited

U.S. PATENT DOCUMENTS

| | | | |
|---|---|---|---|
| 4,085,168 | 4/1978 | Milkovich et al. | 260/886 |
| 4,277,582 | 7/1981 | Mueller et al. | 525/421 |
| 4,300,820 | 11/1981 | Shah | 424/80 |

OTHER PUBLICATIONS

Hasaka et al.
Okano et al.
Nakashima et al.

Primary Examiner—Stanley J. Friedman
Attorney, Agent, or Firm—Alvin Isaacs

[57] ABSTRACT

Novel hydrogel compositions, comprised of a blend of two thermoplastic uncrosslinked polymers, one of which is hydrophobic, and the other hydrophilic, and having a microphase separated morphology are described. These hydrogel compositions are useful as devices for controlling the release rate of bioactive agents, such as therapeutic drugs, antimicrobials, contraceptive agents, or the like, in a biological environment. Depending upon the chemical nature of the agent to be released, its rate of release can be controlled by appropriate selection of the polymeric components of the blend and their relative ratios.

9 Claims, 3 Drawing Figures

MICROPHASE SEPARATED HYDROGELS FOR CONTROLLED RELEASE OF BIOACTIVE MATERIALS

BACKGROUND OF THE INVENTION

This application is a continuation-in-part of pending application Ser. No. 532,643, filed Sept. 15, 1983 now abandoned.

The present invention relates to polymers.

The present invention also relates to hydrogels and water insoluble, but water swellable, crosslinked polymers.

The present invention further relates to microphase separated polymer blend hydrogels.

The present invention most particularly relates to the use of microphase separated polymer blend hydrogels, such as are described in my U.S. Pat. No. 4,300,820, for the controlled release of biologically active materials.

The objective of a controlled release drug or biologically active agent delivery system is to make the drug or agent available at the site of application, i.e. the target organ or tissues, at therapeutically effective concentration levels over a prolonged period of time.

In contrast, conventional oral or intravenous drug administration requires frequent and repeated doses, which result in plasma drug levels that are initially high, but which decrease rapidly due to systemic dilution, metabolic degradation and excretion processes. Further, this pattern produces a time-dependent mixture of desired and undesired effects. These inherent problems associated with the conventional drug administration modes can be greatly minimized in the controlled release drug or agent delivery system of the present invention.

Controlled release drug delivery systems, in general, are comprised of a drug and a polymer, which controls the drug release rate by acting as a diffusion membrane. Most controlled drug release systems can be classified as either monolithic (matrix), reservoir (depot), or combined monolithic-reservoir type devices.

In a matrix release system, the drug is uniformly distributed or dissolved in a polymer.

A reservoir type device consists of a polymeric capsule which is filled with the drug. Release rate of the drug from the matrix system is proportional to the concentration of the drug in the polymer, and therefore it is not constant and follows first order kinetics. On the other hand, reservoir systems are able to produce near constant, i.e. zero order release rates. However, the possibility of catastrophic sudden release due to mechanical failure or a minute hole in the device is a major disadvantage of reservoir type systems.

Hydrogels, which are generally water swollen three-dimensional networks of crosslinked hydrophilic polymers, are especially suitable as membrane and/or matrix materials for controlled drug delivery on account of their excellent biological compatibility, soft and elastomeric character, and high permeability to small molecules.

The nature of the crosslinkages in stable or permanent hydrogels is generally of the covalent type, although ionic crosslinkages in polyelectrolyte complexes are also found. Certain block and graft copolymer hydrogels, possessing a hydrophobic-hydrophilic microphase morphology, have been reported by Milkovich (U.S. Pat. No. 4,085,168), Wichterle (U.S. Pat. No. 4,095,877), Nakashima, et al (J. Biomed. Materials Res., 11, 787 (1977)), and Okano, et al (J. Appl. Polymer Sci, 22, 369 (1978)). In these hydrogels, the hydrophobic and hydrophilic phases are connected to one another by means of covalent bonds.

Controlled release of progesterone, a contraceptive drug, from monolithic hydrogel devices, has been investigated by S. Song ("Hydrogel Devices for Controlled Drug Release", Ph.D. Dissertation, U. of Utah, Utah, 1980."), using homopolymers and copolymers of 2-hydroxyethyl methacrylate, methoxyethyl methacrylate, and methoxyethoxyethyl methacrylate. It was shown that the progestrone release from these hydrogels followed the expected first order kinetics.

Cowsar, et al (ACS Symp. Series 31, Am. Chem. Soc., Washington, D.C. p. 180 (1976)), have reported controlled release of fluoride through poly (2-hydroxyethyl methacrylate) hydrogels for treatment of dental caries.

Hosaka, et al (J. Appl. Polymer Sci., 23, 2089 (1979)), have reported the release rates of erythromycin and erythromycin estolate from hydrogel matrices of N-vinyl pyrrolidone copolymers as a function of the copolymer composition.

Good and Mueller (U.S. Pat. No. 4,277,582) have disclosed a two-component hydrogel system composed of a macromer, such as polyalkylene oxide, having reactive terminal vinyl groups, crosslinked polymers and copolymers of hydrophilic monomers, such as hydroxyethyl methacrylate, vinyl pyrrolidone, etc. The authors have described the use of these two-component hydrogels as carriers for controlled delivery of pharmaceutically active drugs or agents.

Ryde and Ekstedt (U.S. Pat. No. 3,968,201) have claimed compositions in the form of a solid shaped body for the sustained release of medication in the eye. The compositions are comprised of: (a) lipophilic substance, e.g. paraffin wax; (b) a water soluble or swellable polymer, e.g. poly vinyl pyrrolidone, dextran, etc.; (c) water insoluble lipophilic polymer, e.g. polyethylene, copolymer of ethylene and vinyl acetate, poly (butyl methacrylate); and (d) opthalmic drug.

Preparation of tablets, from which the medicinal substance is released at a controlled rate for up to 8 hours, is reported by Hill (U.S. Pat. No. 3,458,622). The medicant in this disclosure is mixed in a blend of polymeric vinyl pyrrolidone with a hydrophilic carboxyvinyl polymer.

As most of the prior art hydrogel compositions, used for controlled drug release, are characterized by a single phase morphology, the release rate of dissolved solutes (active agents) from the matrices of these hydrogels, would by expected to follow first order kinetics, i.e. a continuous decrease with time.

SUMMARY OF THE INVENTION

An object of the present invention is to provide a microphase separated polymeric blend hydrogel.

Another object of the present invention is to provide a microphase separated polymer blend hydrogel for the controlled release of biologically active materials, or the like.

An additional object of the present invention is to control the release rate of an agent over an extended period of time, by suitably varying the chemical compositions and proportions of the polymeric ingredients constituting the hydrogel blends.

Still yet another object of the present invention is to approach near-constant release rates, similar to those of a reservoir device, while retaining the benefit of a matrix system, i.e. avoiding uncontrolled or sudden release due to mechanical rupture or minute hole in the device.

The present invention discloses the use of thermoplastic polymer blend hydrogels, incorporating hydrophilic and hydrophobic microphase domains, as a suitable system for controlled release of biologically active agents, such as therapeutic drugs, antimicrobials, contraceptive agents, insecticides, fungicides, flavors, fragrances, or the like. The controlled release formulation incorporates the active agent, which distributes itself in the two polymeric phases depending upon its partition coefficient.

DESCRIPTION OF THE PREFERRED EMBODIMENTS

The hydrogel compositions of the present invention are suitable for use as devices for the controlled release of drugs and other biologically active agents or releasable materials. They are blends of either a water-soluble homopolymer of N-vinyl lactam, or a water-soluble copolymer of an N-vinyl lactam with 1 to 90 mole percent of copolymerizable monomer containing ethylenic unsaturation, and a water-insoluble copolymer. The latter water-insoluble copolymer may consist of from about 50 to 90 percent by weight, based on the total weight of the copolymer, of a hydrophobic water insoluble ethylenically unsaturated monomer, 2 to 12 percent by weight of an ethylenically unsaturated monomer containing an acid group, and 0 to 50 percent by weight of a hydrophilic ethylenically unsaturated monomer, free from acid groups.

The above blends are further characterized by a microphase separated morphology, in which the major polymeric component forms the continuous phase, and the minor polymeric component forms the dispersed phase.

Figure 1:
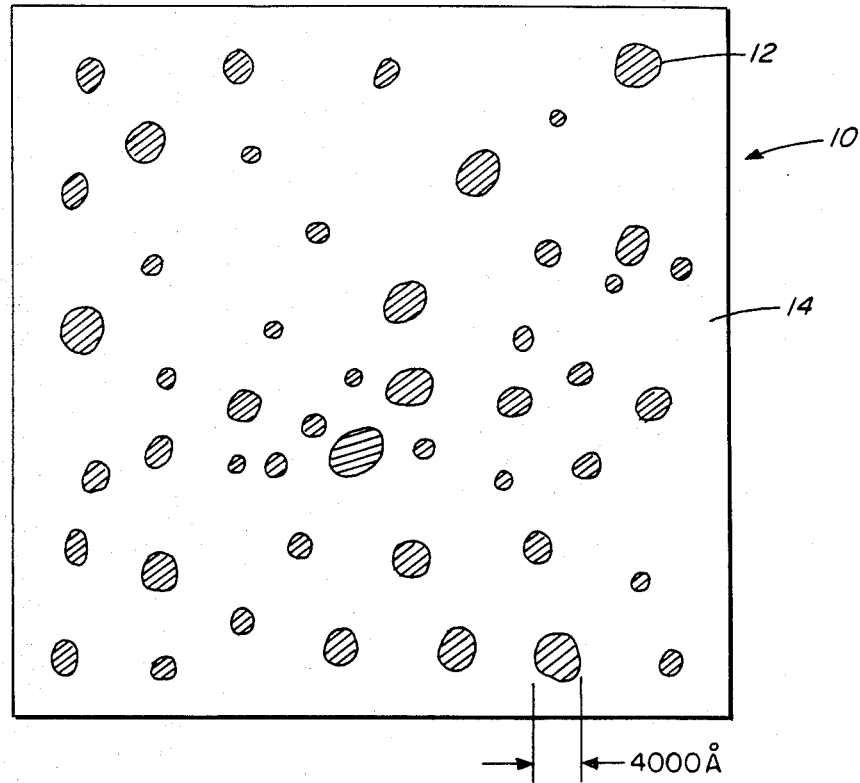
FIG. 1 is a schematic view of the polymer blend morphology of the present invention.

FIG. 1 is a schematic view of the polymer blend morphology of the present invention.

The polymeric blends, depicted generally as 10, are optically clear and substantially free from haziness, indicating that the blends are homogeneous despite the fact that the N-vinyl lactam homopolymer or copolymer is water-soluble and the copolymer is water-insoluble. Examination of the blend morphology at high magnifications with an electron microscope shows the presence of microphase domains (4,000Å or less in diameter), depicted here as 12, of water-insoluble material dispersed in the continuous phase (shown as 14) of water-soluble vinyl lactam polymer or copolymer.

The presence of these microphase domains of the water-insoluble copolymer component prevents dissolution of the continuous phase polymer in water, but unlike covalent cross-linking of polymers, does not render the hydrogel blend non-thermoplastic. Instead, the hydrogel blend possesses the ability to be repeatedly shaped or formed under moderate pressures at a temperature as low as 150° C., or in some cases even lower. The shaped or formed hydrogel composition retains its configuration at room temperature subject to distortion when swollen with water.

The principle of the controlled release bioactive agent delivery system of the present invention, is the utilization of the microphase domains of the dispersed polymeric phase as the depots or reservoirs for the drugs or other material to be released. In an aqueous environment, the hydrated continuous phase serves, in effect, as a membrane for controlling the rate of diffusion of the active agent into the medium surrounding the hydrogel blend material. Thus, the hydrated two-phase polymeric blend serves as a "depot-membrane" system.

If the active agent or drug is highly water soluble, the hydrogel blend composition having the hydrophobic polymeric component as the continuous phase is preferred for controlling the release of the agent over a prolonged period of time. However, in certain circumstances, either polymer may be the continuous phase, depending upon the characteristics of the releasable agent to be delivered. Conversely, in the case of a sparingly water soluble agent or drug, the hydrogel blend composition having a hydrophilic polymeric component as the continuous phase may be preferred for controlling the release of the agent over a prolonged period of time.

In order for this two-phase, hydrophilic-hydrophobic hydrogel polymeric blend to constitute an optimum depot-membrane system, i.e. for achieving zero order kinetics, the chemical nature of the polymeric components of the blend should be such that the partition coefficient of the biologically active agent or drug in the two phases is optimized, i.e. the concentration of the agent in the dispersed phase must be much larger than its concentration in the continuous phase.

Further, depending upon the chemical nature of the active agent or drug or other releasable composition or material, its release rate can be controlled, and may be made to approach zero order kinetics by an appropriate selection of the hydrophobic or hydrophilic characteristics of the polymeric components, and their relative proportions in the blend.

The N-vinyl lactams homopolymers and copolymers, of which can be used in the present invention include those having the structure:

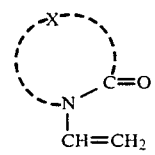

in which X represents an alkylene bridge having three to five carbon atoms, such as 1-vinyl-2-pyrrolidone, 1-vinyl-5-methyl-2-pyrrolidone, 1-vinyl-2-piperidone, and N-vinyl-ε-caprolactam.

The copolymerizable monomers with which the N-vinyl lactams can be copolymerized to form copolymers containing 10 to 99, preferably 25 to 99, mole percent N-vinyl lactam and correspondingly 1 to 90, preferably 1 to 75, mole percent of comonomer, include N,N-dimethyl acrylamide, glyceryl methacrylate, diethylene or triethylene glycol monomethacrylate or other hydrophilic monomers, as well as vinyl acetate, alkyl acrylate or methacrylate, vinyl alkyl ethers, acrylonitrile, vinyl chloride, or other hydrophobic monomers.

In the case of monomers such as vinyl acetate, which themselves form water-insoluble homopolymers, the upper limit of the amount of such monomer which can be employed to form the desired water-soluble copolymer is much lower than in the case of monomers such as N,N-dimethyl acrylamide which form water-soluble homopolymers. These homopolymers and copolymers may have molecular weights from 10,000 to 1,000,000 or more, but those having molecular weights of from about 100,000 to 1,000,000 are preferred. Homopolymers and copolymers of 1-vinyl-2-pyrrolidone are also preferred.

The water-insoluble copolymers which can be employed as blends with the vinyl lactam polymer or copolymer in the compositions of the present invention include water-insoluble copolymers of a hydrophobic water-insoluble ethylenically unsaturated monomer such as alkyl esters of acrylic or methacrylic acid in which the alkyl group has from 1 to 16 carbon atoms, styrene, acrylonitrile, vinyl acetate, vinyl butyrate, vinyl chloride, vinylidene chloride, ethylene, propylene, butylene, butadiene and other polymerizable alkadienes, vinyl alkyl ethers and vinyl alkyl ketones in which the alkyls have 3 or more carbon atoms, and the like.

The copolymers also include as another essential monomer an ethylenically unsaturated monomer containing an acid group such as a carboxylic, sulfonic, or phosphonic acid group; among suitable acidic monomers are acrylic acid, methacrylic acid, crotonic acid, maleic acid, 2-sulfoethyl methacrylate, 1-phenyl vinyl phosphonic acid, and the like. The third monomer, is selected from a group of hydrophilic ethylenically unsaturated monomers, possessing a solubility parameter in excess of 11 $[calories/cm^3]^{\frac{1}{2}}$, free from acidic groups, such as methacrylamide, acrylamide, hydroxyethyl methacrylate, diethylene or triethylene glycol monomethacrylate, glyceryl methacrylate, etc.

In the case of each of the three types of monomers a mixture of two or more individual monomers of the same type can be used.

The relative proportions of the different monomers in the water-insoluble copolymer may vary widely; the hydrophobic water-insoluble ethylenically unsaturated monomer may amout to 50% to 90% by weight, based on the total weight of copolymer, while the ethylenically unsaturated monomer containing an acidic group may amount to 2% to 12% by weight; the hydrophilic ethylenically unsaturated monomer may amount to 0% to 50% by weight. The exact proportions of the three types of monomers are determined by the hydrophobic-hydrophilic balance required in each case. In many cases for attainment of this balance the incorporation of 15% to 45% of a hydrophilic monomer is required.

Thus, in the case of one preferred class of water-insoluble copolymers, the amount of methyl methacrylate (or styrene or 2-ethylhexyl acrylate) is from 55% to 70% by weight based on the total copolymer weight, the amount of acrylic acid is from 2% to 12% by weight, and the amount of methacrylamide is from 25%-43% by weight.

In the case of another preferred water-insoluble copolymer, the amount of n-butyl methacrylate is from 55% to 80% by weight based on the total copolymer weight, the amount of acrylic acid is from 2% to 12% by weight, and the amount of methacrylamide is from 15% to 35% by weight.

In the case of still another preferred water-insoluble copolymer, the amount of methyl methacrylate is from 88 to 90% by weight of the total copolymer, while 2-acrylamido-2-methyl propanesulfonic acid, the only other monomer constituent, is from 10%-12% by weight. In this case, the presence of a non-acidic hydrophilic comonomer is not essential.

In the case of still another preferred water-insoluble copolymer, the amount of n-butyl methacrylate is from 50 to 78% by weight of the total copolymer, the amount of acrylic acid is from 2 to 12% by weight, and the amount of hydrophilic p-styrene sulfonamide is from 20% to 35% by weight. In another preferred water-insoluble copolymer, the amount of n-butyl methacrylate is from 55% to 70% of the total copolymer weight, acrylic acid is from 2 to 12%, and hydroxyethyl methacrylate is from 25% to 43%.

The relative proportions of the water-soluble polymer or copolymer and of the water-insoluble copolymer in the blend may vary over a wide range, i.e. from about 10 to 90 percent, based on the total weight of the blend, of the former or the latter polymeric component. The optimum proportions of each component within the above range will vary, depending upon the partition coefficient of the drug or active agent; the desired release rate; overall solubility of the agent in the blend; and, the solubility of the agent in the environmental aqueous fluid.

The partition coefficient of the agent or drug in the two phases, i.e. continuous and dispersed, can be affected by, not only the chemical compositions of the two polymeric components, but also by the optional inclusion in the polymer blend of a compatible, water soluble liquid plasticizer, such as ethylene glycol, diethylene glycol, glycerine, or liquid poly (ethylene oxides).

Further, the amount of the optional water soluble plasticizer may vary from 0 to 50 parts per 100 parts, preferably from 0 to 40 parts, by combined weights of the polymeric components.

Additionally, the active agents compositions or materials which may be incorporated for release should preferably be non-polymeric, and not be strongly acidic or basic. Active agents, that are capable of interacting strongly with the polymeric components of the hydrogel blend, will not be released easily, and may even interfere with the formation of the desired microphase morphology in the hydrogel blend.

The amount of the releasable active agent incorporated in the hydrogel blend varies widely, depending upon the particular agent, the desired biological activity, and the time period over which the agent is to be released. Concentration of the active agent in the hydrogel blend will preferably be less than 30 percent by weight of the hydrogel blend. High loading levels of the agent are likely to adversely affect desired microphase morphology of the hydrogel blend and its resultant release rates.

Many of the therapeutic drugs suitable for controlled release are found in U.S. Pat. No. 4,277,582 (columns 10 and 11) and U.S. Pat. No. 3,732,865 (columns 10 and 11). In addition, birth control agents, such as anti-fertility drugs (e.g. progesterone, levonorgestrel, ethinyl estradiol, etc.) and spermicides, e.g. nonoxynol-9, urea, and Gossypol (a polyphenolic pigment extracted from the cotton plant), antimicrobials, fragrances, flavors, fluorides, as well as fungicides, insecticides, herbicides and other pest control agents may also be suitably incorporated into the hydrogel compositions of this invention. Other examples of biologically active agents that may be suitable for use in this invention are found in U.S. Pat. No. 3,660,563 (see columns 3 to 7).

It is also envisioned that the present invention may be suitably utilized for the controlled release of non-bioactive chemicals or other substances in a nonbiologic and/or industrial application. An envisioned instance is the controlled release of a catalytic agent into a reaction mixture.

Further, the hydrogel blend containing the active agent may be prepared by dissolving the agent together with the polymeric components of the blend in suitable solvent, such as 2-methoxyethanol, N,N-dimethylformamide, or methanol, and then removing the solvent by evaporation, preferably under vacuum at 60° C. to 100° C.

Additionally, the hydrogel blend containing the releasable agent may be fabricated into a desired configuration or device (such as film, tubing, rod, etc.) by a process of melt extrusion, molding or solution casting.

Further, the composition may also be coated onto a variety of substrates having the desired shape or structure.

In the case of drugs, the controlled release hydrogel compositions and/or devices are ideally suited for application in body cavities such as oral, occular, vaginal and rectal. Further, films of the hydrogel blend containing certain drugs such as nitroglycerine, may be suitable for transdermal delivery or absorption through mucous membrane of the mouth, such as that of the buccal cavity.

Figure 2:
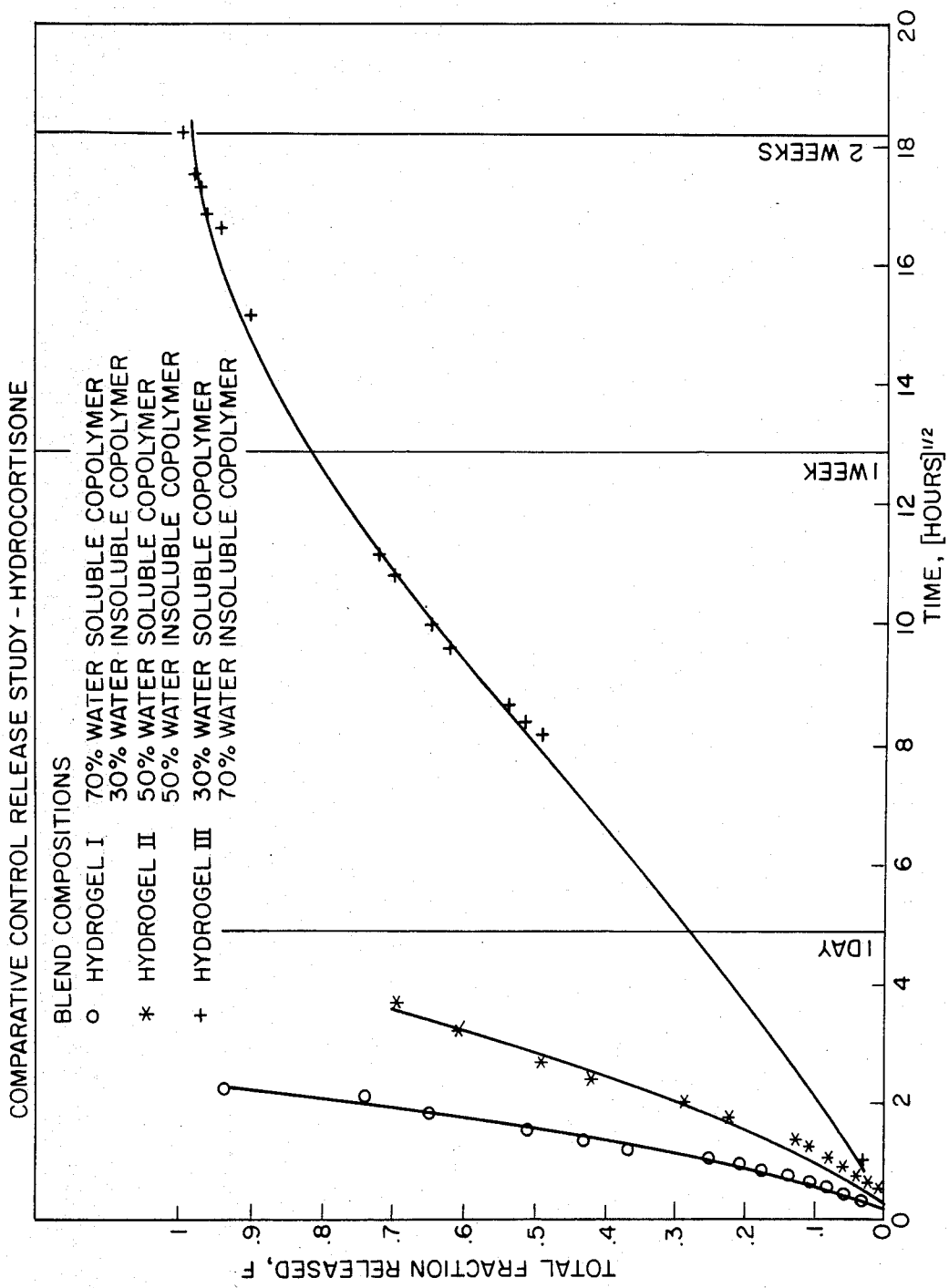
FIG. 2 is a graphical depiction of the comparative release rates of hydrocortisone from varying hydrogel compositions of the present invention.

FIG. 2 is a graphical depiction of the comparative release rates of hydrocortisone from varying hydrogel compositions of the present invention.

Figure 3:
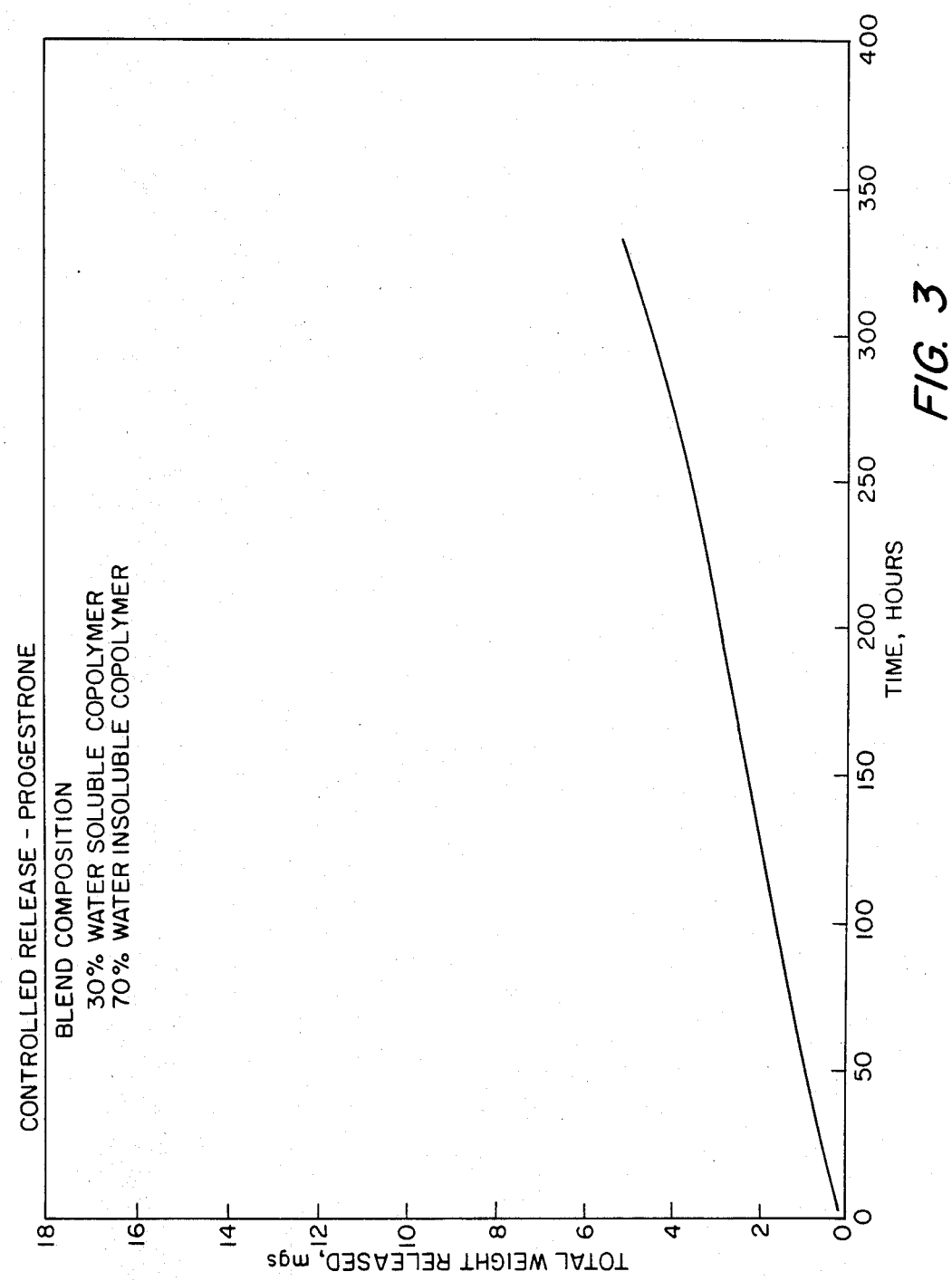
FIG. 3 is a graphical depiction of release rates of progesterone from an exemplary embodiment of present invention.

FIG. 3 is a graphical depiction of release rates of progesterone from an exemplary embodiment of present invention.

In the particular agents studied, the most dramatic change, i.e. decrease in the release of hydrocortisone was observed when the proportion of the water soluble copolymer in the hydrogel blend decreased from 50 to 30 percent. These results may be interpreted in terms of the microphase morphology of the blend, and relative solubilities, i.e. partition coefficient, of hydrocortisone in the polymeric components of the blend.

Hydrocortisone being water-soluble, it is expected to be relatively more soluble in the water-soluble copolymer than in the water-insoluble copolymer.

Of the three blend compositions studied, only the one containing 30 percent of the water-soluble copolymer may have the copolymer as the dispersed phase. Consequently, microphase "depots" of hydrocortisone are likely only in this composition, where the continuous phase of the water-insoluble copolymer is available as the rate controlling membrane. In the other two compositions, hydrocortisone is released from a matrix of the water-soluble copolymer forming the continuous phase. Therefore, the release rate of hydrocortisone was considerably slower in the former case than in the latter two cases.

The present invntion is further exemplified below by several examples thereof in accordance with the preferred embodiments of the invention. However, it is understood that the invention is not limited to the examples included, but that equivalents will be apparent to those skilled in the art, and disclosed herein.

EXAMPLES

Release rates of two steroids, i.e. hydrocortisone and progesterone, from polymer blend hydrogels upon equilibration in a large excess of water were studied as a function of time. In each case the proportion of the steroid was 10% based on the combined weight of the steroid and the polymeric components, which were (i) a water soluble copolymer containing 30 and 70 mole percent of N-vinyl 2-pyrrolidone and N,N-dimethylacrylamide, respectively; and (ii) a water-insoluble copolymer of 73 percent by weight of n-butyl methacrylate, 22 percent by weight of methacrylamide, and 5 percent by weight of acrylic acid, based on total weight of the copolymer, as shown in FIGS. 2 and 3.

The hydrogel polymeric blends containing the steroids were prepared in a manner described earlier, and as disclosed in U.S. Pat. No. 4,300,820, employing 2-methoxyethanol as a solvent. Circular discs—$\frac{3}{4}''$ in diameter and 0.026" in thickness were prepared by a conventional process of compression molding at 350° F.

In each case the disc was placed in approximately 500 ml of distilled water at 22° C. under continuous gentle agitation. Release rates of the steroid was followed by determining the change in its concentration, monitored by ultraviolet spectroscopy, in the surrounding aqueous medium.

EXAMPLE 1

Hydrocortisone

Release rates (see FIG. 2) of a relatively water soluble drug, such as hydrocortisone, varied from hours, in the case of the more hydrophilic blend (70 percent water soluble copolymer) to two weeks, in the case of the less hydrophilic blend (30 percent water soluble copolymer).

EXAMPLE 2

Progesterone

Release rates (See FIG. 3) of progesterone which is less water soluble than hydrocortisone from the hydrogel blend containing 30 percent water soluble copolymer were followed for 2 weeks, during which time approximately 30 percent of the steroid contained, therein, was released gradually. wherein said bioactive agent is incorporated in and releasable from a depot-membrane system.

I claim:

1. A composition for the controlled and consistent release of a water-soluble drug comprising a blend of:
   10 to 30% by weight of a non-crosslinked water-soluble homopolymer of N-vinyl lactam having the structure

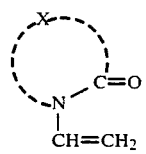

in which X represents an alkylene bridge having three to five carbon atoms, or a water-soluble copolymer thereof with 1 to 90 mole percent of copolymerizable monomer containing a polumerizable ethylenic unsaturation;

90 to 70% by weight of a non-crosslinked water-insoluble copolymer comprising from about 50 to 90 percent by weight, based on the total weight of the copolymer, of a hydrophobic water-insoluble ethylenically unsaturated monomer, 2 to 12 percent by weight of an ethylenically unsaturated monomer containing an acid group, and 0 to 50 percent by weight of a hydrophilic ethylenically unsaturated monomer, free from acid groups;

and less than 30% by weight, based on the weight of said blend, of a water-soluble drug dispersed throughout said blend.

2. A composition as claimed in claim 1 in which said water-soluble polymer is a homopolymer of N-vinyl-2-pyrrolidone.

3. A composition as claimed in claim 1 in which said water-soluble drug is hydrocortisone or progesterone.

4. A composition as claimed in claim 1 in which said water-soluble polymer is a homopolymer of N-vinyl-2-pyrrolidone, and said water-insoluble copolymer is a copolymer of 73% by weight of n-butyl methacrylate, 22% by weight of methacrylamide, and 5% by weight of acrylic acid.

5. A composition as claimed in claim 4 in which said drug is hydrocortisone or progesterone.

6. A composition for the controlled and consistent release of a water-soluble drug comprising a blend of:

10 to 30% by weight of a non-crosslinked water-soluble copolymer of N-vinyl lactam having the structure

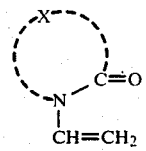

in which X represents an alkylene bridge having three to five carbon atoms, with 1 to 90 mole percent of copolymerizable monomer containing a polymerizable ethylenic unsaturation;

90 to 70% by weight of a non-crosslinked water-insoluble copolymer comprising from about 50 to 90 percent by weight, based on the total weight of the copolymer, of a hydrophobic water-insoluble ethylenically unsaturated monomer, 2 to 12 percent by weight of an ethylenically unsaturated monomer containing an acid group, and 0 to 50 percent by weight of a hydrophilic ethylenically unsaturated monomer, free from acid groups;

less than 30% by weight, based on the weight of said blend, of a water-soluble drug; and said water-soluble and water-insoluble copolymer components and said water-soluble drug, being dispersed throughout said blend.

7. A composition as claimed in claim 6 in which said water-soluble polymer is a copolymer of 30 mole percent N-vinyl-2-pyrrolidone and 70 mole percent of N,N-dimethylacrylamide, and said water-insoluble copolymer is a copolymer of 73% by weight of n-butyl methacrylate, 22% by weight of methacrylamide, and 5% by weight of acrylic acid.

8. A composition as claimed in claim 7 in which said drug is hydrocortisone or progesterone.

9. A composition as claimed in claim 6 in which said water-soluble polymer is a copolymer of 30 mole percent N-vinyl-pyrrolidone and 70 mole percent of N,N-dimethlacrylamide.

* * * * *